United States Patent [19]

Koziol et al.

[11] Patent Number: 4,838,266

[45] Date of Patent: Jun. 13, 1989

[54] LENS SHAPING DEVICE USING A LASER ATTENUATOR

[76] Inventors: Jeffrey E. Koziol, 5 Dogwood, Rolling Meadows, Ill. 60008; Gholam A. Peyman, 123 Walnut St., New Orleans, La. 70118

[21] Appl. No.: 251,522

[22] Filed: Sep. 30, 1988

Related U.S. Application Data

[63] Continuation-in-part of Ser. No. 904,408, Sep. 8, 1986, abandoned.

[51] Int. Cl.$^4$ ............................................. A61N 5/06
[52] U.S. Cl. ................................ 128/303.1; 128/395; 350/311
[58] Field of Search ...................... 128/303.1, 395, 362; 350/311, 312, 314

[56] References Cited

U.S. PATENT DOCUMENTS

| | | | |
|---|---|---|---|
| 988,710 | 4/1911 | Holbrook | 350/314 |
| 1,332,410 | 3/1920 | Potts | 350/314 |
| 1,900,966 | 3/1933 | Wolfe | 350/314 |
| 1,963,110 | 6/1934 | Assael | 350/311 |
| 2,286,219 | 6/1942 | Martinek | 350/311 |
| 2,356,694 | 8/1944 | Potter et al. | 350/314 |
| 2,384,578 | 9/1945 | Turner | 350/314 |
| 2,474,828 | 7/1949 | Connelly et al. | 350/314 |
| 3,597,046 | 8/1971 | Smithgall | 350/311 |
| 3,843,235 | 10/1974 | Mino et al. | 350/314 |
| 4,461,294 | 7/1984 | Baron | 128/303.1 |
| 4,469,098 | 9/1984 | Davi | 128/303.1 |
| 4,648,400 | 3/1987 | Schneider et al. | 128/303.1 |

FOREIGN PATENT DOCUMENTS

| | | | |
|---|---|---|---|
| 44-5592 | 3/1969 | Japan | 350/314 |
| 25026 | 8/1970 | Japan | 350/314 |
| 21256 | 2/1979 | Japan | 350/314 |
| 22844 | 2/1979 | Japan | 350/311 |
| 38701 | 3/1984 | Japan | 350/311 |
| 33976 | 2/1951 | Poland | 350/312 |

OTHER PUBLICATIONS

J. Taboada et al., "Response of the Corneal Epithelium to KrF Excimer Laser Pulses", *Health Physics*, vol. 40, May 1981, pp. 677–683.

L. J. Girard, "Advanced Techniques in Ophthalmic Microsurgery", *Corneal Surgery*, vol. 2, 1981, Chapters 3–6.

D. F. Muller et al., "Studies of Organic Molecules as Saturable Absorbers at 193 nm", *IEEE Journal of Quantum Electronics*, vol. QE–18, No. 11, Nov. 1982, pp. 1865–1870.

K. Bennett et al., "Variable Laser Attenuators–Old and New", *Laser Focus*, Apr. 1983.

S. L. Trokel et al., "Excimer Laser Surgery of the Cornea", *Am. J. of Ophthalmology*, vol. 96, Dec. 1983, pp. 710–715.

A. M. Cotliar et al., "Excimer Laser Radial Keratotomy", *Ophthalmology*, vol. 92, No. 2, Feb. 1985, pp. 206–208.

C. A. Puliafito et al., "Excimer Laser Ablation of the Cornea and Lens", *Ophthalmology*, vol. 92, No. 6, Jun. 1985, pp. 741–748.

*Primary Examiner*—Lee S. Cohen
*Assistant Examiner*—David Shay
*Attorney, Agent, or Firm*—Roylance, Abrams, Berdo & Goodman

[57] ABSTRACT

A device for modifying the surface of an optical element including a laser beam and a laser energy attenuator. The attenuator varies the energy distribution of the laser beam radially of the beam, thereby etching the surface of the optical element in conformance with the varied energy distribution. In one embodiment, the attenuator includes a positive lens-shaped portion with a laser energy absorbing material therein, which results in etching a positive lens shape on the optical element. In a second embodiment, the attenuator includes a negative lens-shaped portion with a laser energy absorbing material therein, which results in etching a negative lens shape on the optical element. End caps for each of the positive and negative shaped portions have planar outer surfaces and the same refractive indexes as those portions, thereby preventing refraction of the laser beam upon its passing through the attenuator. The attenuator can be cooled as it absorbs the energy from the laser.

23 Claims, 2 Drawing Sheets

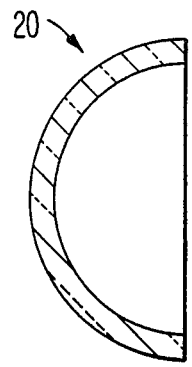
FIG. 1.
FIG. 2.
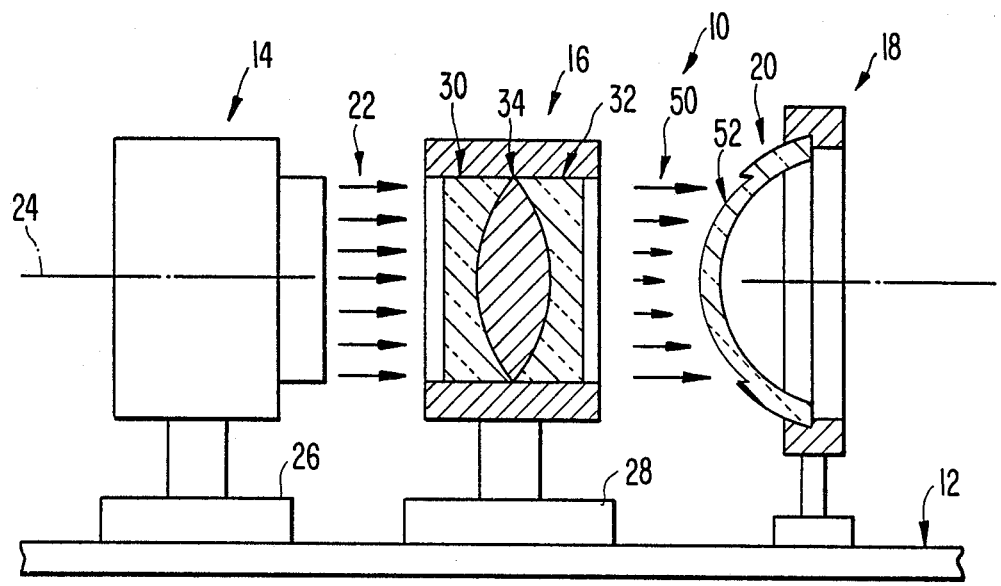
FIG. 3.
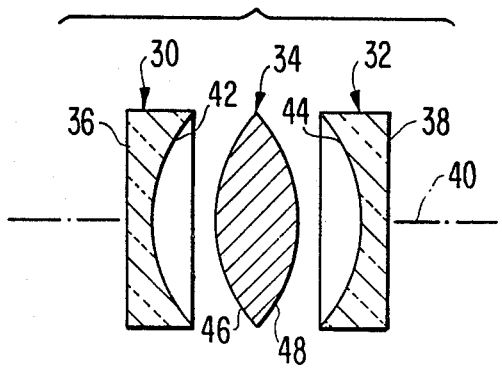
FIG. 4.
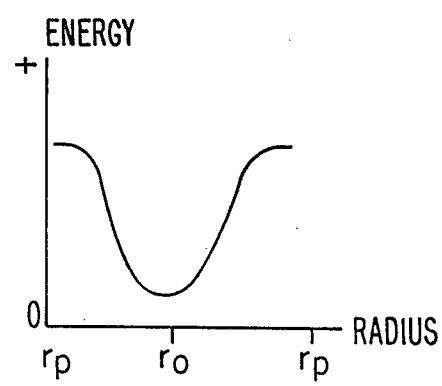

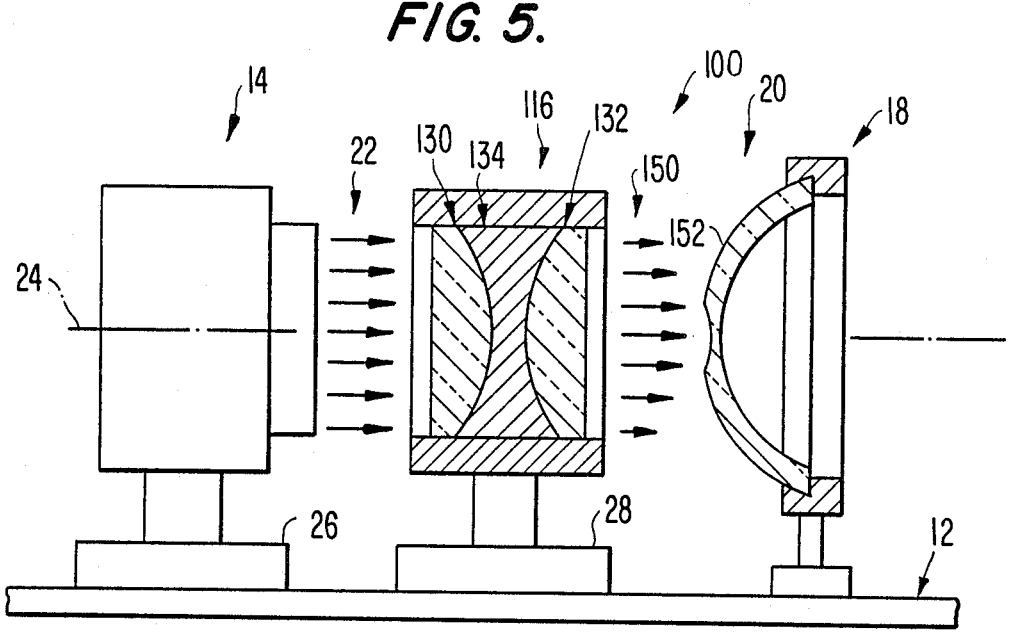
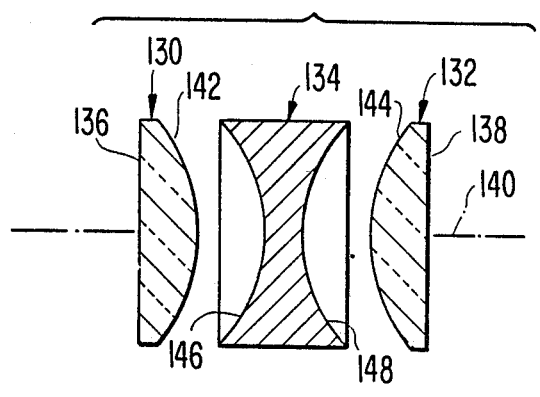
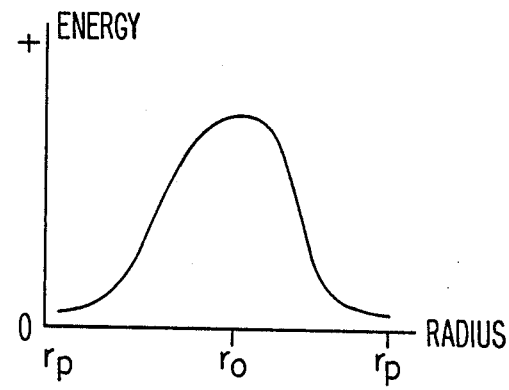
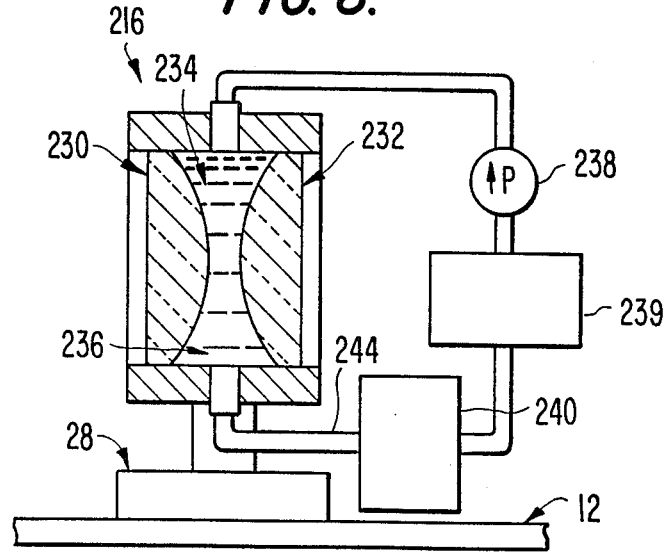

LENS SHAPING DEVICE USING A LASER ATTENUATOR

RELATED APPLICATION

This application is a continuation-in-part of U.S. patent application Ser. No. 06/904,408 filed Sept. 8, 1986, now abandoned.

FIELD OF THE INVENTION

The invention relates to a device and method for shaping the surface of an optical element. More particularly, the invention relates to the use of a laser beam and a laser energy attenuator for modifying the refractive power of an optical lens by varying the energy distribution of the laser beam radially thereof by absorbing part of the energy in the beam.

BACKGROUND OF THE INVENTION

There is widespread interest in ophthalmology to change the refractive state of the eye itself. The human eye has a strength of 60 diopters with the cornea supplying on the average two-thirds, or 40 diopters, of strength. The remaining power of 20 diopters resides in the lens of the eye. Thus, the living cornea itself contributes significantly to the focusing of light by the eye.

Consequently, it is not surprising that attempts to change the refractive state of the eye, that is to eliminate nearsightedness, farsightedness, or astigmatism, have concentrated on changing the shape of the cornea. This is the most accessible portion of the eye and the one with the most refractive power. In this regard, 99% of all refractive error lies between zero and ±20 diopters, and 95% between zero and ± seven diopters.

Current procedures do exist that change the shape of the cornea. For example, radial keratometry involves making radial cuts in the cornea to flatten or reduce corneal power. Other procedures involve removing part of the cornea, lathing it to a new shape, and suturing it back in place.

In addition, the use of the excimer laser has been proposed to change the shape of the cornea either by direct or indirect lathing of the cornea or by using the laser beam to make radial incisions. The ultraviolet light of the excimer laser is completely absorbed by biological tissue such as the cornea, and upon such absorption photoablation takes place. This is the disintegration of tissue without deleterious thermal effects. Using this laser energy, it is possible thereby to remove in tact corneal tissue for the human eye layer by layer and thereby change its refractive power.

However, to date these various procedures have had numerous shortcomings. For example, the radial keratometry procedure is not exact and often the change in curvature of the cornea is not precisely accomplished. Additional side effects from this procedure are also recorded wherein patients have an oversensitivity to natural light.

Moreover, when using excimer lasers, it is very difficult to precisely control the laser energy and if this is not done, the ablated corneal surface will be changed irregularly and vision worsened.

Examples of publications dealing with attenuation of lasers, photoablation of corneas and other treatments thereof are as follows: J. Taboada et al, "Response of the Corneal Epithelium to KrF Excimer Laser Pulses", *Health Physics*, Vol. 40, May 1981, pp. 677–683; L. J. Girard, "Advanced Techniques in Ophthalmic Microsurgery", *Corneal Surgery*, Vol. 2, 1981, Chapters 3–6; D. F. Muller et al, "Studies of Organic Molecules as Saturable Absorbers at 193 nm", *IEEE Journal of Quantum Electronics*, Vol. QE-18, No. 11, November 1982, pp. 1865–1870; K. Bennett et al, "Variable Laser Attenuators—Old and New", *Laser Focus*, April 1983; S. L. Trokel et al, "Excimer Laser Surgery of the Cornea", *Am. J. of Ophthalmology*, Vol. 96, December 1983, pp. 710–715; A. M. Cotliar et al, "Excimer Laser Radial Keratotomy", *Ophthalmology*, Vol. 92, No. 2, February 1985, pp. 206–208; and C. A. Puliafito et al, "Excimer Laser Ablation of the Cornea and Lens", *Ophthalmology*, Vol. 92, No. 6, June 1985, pp. 741–748.

Examples of U.S. patents relating to laser surgery include U.S. Pat. Nos. 4,461,294 to Baron and 4,469,098 to Davi, the disclosures of which are hereby incorporated by reference.

SUMMARY OF THE INVENTION

Accordingly, a primary object of the invention is to provide a device and method for shaping a live cornea in a precise and accurate manner to change the overall refractive power of the eye.

Another object of the invention is to provide a device and method for modifying the surface of a live cornea or any other optical element in a precise and accurate manner to vary the refractive power of the cornea or element.

A further object of the invention is to provide a device and method for modifying the surface of an optical lens to vary its refractive power by using a laser energy attenuator capable of varying the energy distribution of the laser beam radially thereof.

A further object of the invention is to provide such a device and method that utilizes a laser attenuator, which maintains the rays of the laser beam in a parallel configuration therethrough, and uses a positively or negatively lens-shaped laser energy absorbing optical element.

The foregoing objects are basically attained by providing a device for modifying the surface of an optical element to vary its refractive power, the combination comprising a means for generating a laser beam, the laser beam having a central axis and an outer periphery; a laser energy attenuator, aligned to intercept the laser beam, for varying the energy distribution of the laser beam between the central axis and the outer periphery of the laser beam; and a means for supporting the optical element in a position to intercept the laser beam after the laser beam has been intercepted by the laser energy attenuator means.

The foregoing objects are also attained by providing a method of modifying the surface of an optical element to vary its refractive power, comprising the steps of generating a laser beam having a central axis and an outer periphery, varying the energy distribution of the laser beam between the central axis and the outer periphery thereof, and intercepting the varied laser beam with the optical element.

In more detail, the laser energy attenuator for varying the energy distribution of the laser beam radially thereof comprises a first optical portion, a second optical portion and a central optical portion located between the first and second portions, the central optical portion capable of absorbing laser energy.

Other objects, advantages and salient features of the invention will become apparent from the following detailed description, which, taken in conjunction with the annexed drawings, disclosed preferred embodiments of the invention.

DRAWINGS

Referring now to the drawings which form a part of this original disclosure:

FIG. 1 is a side elevational view in longitudinal section of an untreated optical element in the form of a lens, either a cornea or an inorganic lens;

FIG. 2 is a side elevational view in partial longitudinal section showing the device in accordance with the invention including a laser, a laser energy attenuator using a positive lens-shaped absorbing optical portion, and a lens located in a lens support, the lens having been modified upon exposure to the laser energy via the attenuator;

FIG. 3 is an exploded, side elevational view in longitudinal section of the main parts of the laser energy attenuator in FIG. 2 including the first and second optical portions and the positive lens-shaped central absorbing optical portion therebetween;

FIG. 4 is a graph of the energy distribution of the laser beam as it exits the laser energy attenuator showing the distribution of the energy thereof as a function of the distance between the central axis $r_o$ of the attenuator and the radial periphery $r_p$ thereof;

FIG. 5 is a side elevational view in partial longitudinal section of a second embodiment of the device in accordance with the invention showing a laser, a modified laser energy attenuator using a negative lens-shaped absorbing optical portion, and a lens located in a support, the lens surface having been modified upon exposure to the laser energy via the attenuator;

FIG. 6 is an exploded, side elevational view in longitudinal section of the main parts of the laser energy attenuator seen in FIG. 5 including the first and second optical portions and the negative lens-shaped central absorbing optical portion located therebetween;

FIG. 7 is a graph of the energy distribution of the laser energy in FIG. 5 leaving the attenuator as a function of the distance between the central axis $r_o$ of the attenuator and the radial periphery $r_p$ thereof; and FIG. 8 is a side elevational view in longitudinal section of a further modified laser energy attenuator wherein the central absorbing portion is hollow and receives an energy absorbing liquid therein, which is cooled to in turn cool the attenuator.

DETAILED DESCRIPTION OF THE INVENTION

Referring to FIGS. 1-4, the device 10 in accordance with the invention comprises a base 12 supporting a laser 14, a laser energy attenuator 16, and a lens support 18 in which the optical element in the form of lens 20 is located. As seen in FIG. 1, the lens 20 is untreated, while in FIG. 2 it has been treated by the device 10 so that its surface is modified, thereby modifying its refractive power. As shown in FIGS. 1-4, the laser energy attenuator 16 shapes the energy distribution of the laser beam output from laser 14 so that the thickness of the treated lens decreases as the radius increases from the center thereof. Thus, the attenuator varies the radiative flux density of the laser energy striking the lens 20 to in turn vary its surface and thus its thickness and refractive power.

The laser 14 is a conventional excimer laser preferably generating a monochromatic parallel-ray light beam 22 of uniform energy in the ultraviolet portion of the spectrum. On the other hand, lasers of different frequencies can be used, such as in the infrared part of the spectrum. The laser beam 22 has a central axis 24 which is aligned with and coaxial with the central axes of the attenuator 16, lens 20 and lens support 18 so that the laser beam is intercepted by the attenuator and lens. As shown in FIG. 2, the outer periphery of the laser beam 22 is substantially the same as the outer periphery of the main parts of the attenuator. If necessary, the outer periphery or diameter of the laser beam can be made smaller by use of a diaphragm or other similar device. The laser 14 is supported on base 12 via support 26.

The laser energy attenuator 16 comprises a support 28 located on base 12, a first optical portion 30, a second optical portion 32, and a central optical portion 34 located between the first and second portions. The three optical portions are coaxially aligned and have their central axes aligned with the central axis 24 of the laser. These three optical portions can be formed of quartz, plastic or glass and each has the same refractive index. The outer surfaces of the first and second portions are planar, parallel and perpendicular to their central axes. Thus, the laser beam passing therethrough will maintain its parallel beam configuration and not be refracted outwardly or inwardly within the attenuator 16.

As seen in FIG. 3, the first and second optical portions 30 and 32 act as end caps for the central optical portion, with the first and second portions having outer surfaces that are planar, parallel to one another, and perpendicular to the central axis 40 thereof. The inner surfaces 42 and 44 of the first and second optical portions are concave and the opposed, regular outer surfaces 46 and 48 of the central optical portion 34 are convex with the same radius of curvature as each other and as the inner surfaces 42 and 44 of the first and second optical portions. The outer peripheries of these three optical portions are preferably cylindrical.

Thus, the central optical portion 34 is bi-convex, and each of the first and second optical portions 30 and 32 are plano-concave. In essence, the central optical portion 34 is in the shape of a negative optical lens.

As used herein regarding the shape of the central optical portion in FIGS. 1-4, as well as FIGS. 5-7 and FIG. 8, "lens" means an optical portion that has two opposite regular surfaces either both curved or one curved and the other plane and that is used either singly or combined in an optical instrument for forming an image by focusing rays of light.

The first and second optical portions 30 and 32 are formed from material that is transparent to the laser beam energy, while the central optical portion 34 is uniformly formed from or has uniformly therein material that absorbs the laser energy from laser 14. Normally, the material uniformly absorbs the energy from the laser. However, since the thickness of the central optical portion 34 varies, i.e., reduces from the central axis to the outer radial periphery thereof, the amount of laser energy absorbed likewise varies in a symmetrical pattern from the central axis. This is illustrated in the graph of FIG. 4 wherein more laser energy passes through the central optical portion 34 at the radial periphery than at the central axis. Forming an optical device with laser energy absorbing material is known in the art and examples of these materials are as follows: (2,2 dichlorocyclopropyl)benzene; p-phenylazoanaline; acetophenone; methyl benzoate; 1,4 napthoquinone; 1,2 napthoquinone; anthraquinone; ferrocene; ferrocenecarboxylic acid; 1,1' ferrocenedicarboxylic acid; ferrocenecarboxaldehyde; catechol; resorcinol; hydroquinone; 1,2,4-benzenetriol; 2-methyl-resorcinol; 3-methyl-catechol; methylhydroquinone; 4-methyl-catechol; phenyl boric acid; p-bromo-phenylboric acid; (1-methylbutyl)-benzene; and cyclopropylbenzene.

As seen in FIG. 2, the lens support 18 supports lens 20 therein in a position aligned with and coaxial with the central axis 24 of the laser and the central axis of the attenuator 16 so that the lens 20 intercepts the laser beam 50 as it exits the attenuator 16.

The lens 20 can be formed from organic material such as a live cornea or a frozen donor cornea which are photoablated by the laser. Alternatively, the lens 20 can be formed from inorganic material such as plastic, quartz or glass which are etched by the laser.

In operation, once the lens 20 is positioned in support 18 and the laser 14 activated, the parallel rays of laser beam 22 exit the laser and are intercepted by the attenuator 16. The arrows designating the laser beam 22 in FIG. 2 are shown as having the same length which indicates the same energy distribution from the central axis of the laser beam to the outer periphery thereof.

The laser beam 22 then passes through the transparent first optical portion 30 and is intercepted by the central absorbing optical portion 34. The energy distribution of the laser beam 22 is thereby varied and, in this case, more energy is transmitted near the center of optical portion 34 than at the outer radial periphery. The laser beam then passes out of the central optical portion 30 and through the transparent second optical portion 32 and is intercepted by the lens 20. The altered laser beam 50 shown in FIG. 2 is represented by arrows having a smaller length closer to the central axis to reflect its energy distribution. Since the energy of the beam 50 is greater at the periphery, it etches or photoablates more of the lens 20 in the outer peripheral areas as shown in FIG. 2 as modified surface 52. As seen therein, the refractive power of lens 20 has been converted into a more positive lens due to the varied energy distribution of the laser beam 50.

To adjust the absorption of the laser energy by the central portion and thus modify the etching or photoablation of lens 20; the profile of the central portion can be varied, which is like varying the power of a positive or negative lens. The shape of the central portion can be varied precisely using a lathe or different molds. In addition, the overall energy of the laser can be varied uniformly by varying the energy of each pulse or the number of pulses per second to increase or decrease the overall effect on the lens.

EMBODIMENT OF FIGS. 5-7

As seen in FIGS. 5-7, a modified device 100 in accordance with the present invention is shown where the laser attenuator 116 is modified while the laser 14, support 18 and base 12 remain the same. In this embodiment, the laser attenuator 116 has a negative lens-shaped absorbing central optical portion and thereby provides a photoablation or etching of lens 20 wherein the thickness of the lens is less adjacent the central axis thereof.

In particular, laser attenuator 116 comprises first optical portion 130, second optical portion 132, and central optical portion 134 located therebetween, each having the same refractive index and being coaxial along axis 140. The first and second optical portions are transparent to the laser energy from laser 14 as in FIGS. 2-4 while the central absorbing optical portion 134 has material therein to absorb the laser energy as described above regarding FIGS. 2-4. In this case, the first optical portion 130 is plano-convex and thus has a planar outer surface 136 and a convex inner surface 142. Likewise, the second optical portion 132 is plano-convex and has a planar outer surface 138 and a convex inner surface 144. The central optical portion 134 is bi-concave and comprises inner concave surfaces 146 and 148.

In this embodiment, laser beam 22 seen in FIG. 5 passes through the attenuator 116 and emerges as modified laser beam 150 whose energy is greater at the center and lesser at the radial periphery as illustrated by the decreasing length of the arrows representing laser beam 150. Thus, the modified lens surface 152 on lens 20 is thinner near the central axis than radially thereof. Thus, by using an absorbing central optical portion 134 in the form of a negative lens, the lens 20 is modified so that its refractive power is more negative. This is illustrated in FIG. 7 where the energy of laser beam 150 is greater at the central axis thereof and lesser adjacent the outer periphery thereof.

EMBODIMENT OF FIG. 8

In FIG. 8, a further modified laser energy attenuator 216 is illustrated wherein first and second optical portions 230 and 232, which are plano-convex, define a space 234 therebetween in the form of a bi-concave cavity. This cavity receives a liquid 236 therein which has laser energy absorbing material therein and thereby acts as a central absorbing optical portion. In order to cool this liquid and the absorber formed thereby, the liquid is circulated from reservoir 240 through a suitable heat exchanger 239 via pump 238 and conduits 242 and 244, which are connected with the support 28 for the attenuator. While FIG. 8 shows the central absorbing cavity in the form of a negative lens, it could also be in the form of a positive lens.

Thus, FIG. 8 illustrates the device in accordance with the invention wherein the attenuator is cooled as it absorbs energy from the laser. In addition, the embodiments of the invention shown in FIGS. 2-4 and 5-7 could also be cooled in any desired manner as necessary.

As seen in FIG. 8, the liquid 236 has the same refractive index as the first and second optical portions 230 and 232 to avoid refraction of the laser beam passing through attenuator 216.

While various advantageous embodiments have been chosen to illustrate the invention, it will be understood by those skilled in the art that various changes and modifications can be made therein without departing from the scope of the invention as defined in the appended claims. For example, not only positive and negative lens-shaped central absorbing portions can be used, but also such a central absorbing portion in the shape of an astigmatic lens could be utilized to correspondingly modify the target lens. In addition, while the lens-shaped central absorbing portions shown in the drawings have two curved opposite surfaces, these surfaces could also comprise one planar surface and one curved surface.

What is claimed is:

1. A device for modifying the surface of an optical element to vary its refractive power, the combination comprising:

means for generating a laser beam, said laser beam having a central axis and an outer periphery;

laser energy attenuator means, aligned to intercept said laser beam, for varying the energy distribution of said laser beam between said central axis and said outer periphery of said laser beam without refracting said laser beam within said laser energy attenuator means; and means for supporting the optical element in a position to intercept said laser beam after said laser beam has been intercepted by said laser energy attenuator means, said laser energy attenuator means including a laser energy absorbing optical lens-shaped portion having a central axis, and having an axial thickness that varies radially of said central axis thereof in a predetermined manner in proportion to the desired change in refractive power of the optical element.

2. A device according to claim 1, wherein said laser energy absorbing optical lens-shaped portion is in the shape of a positive optical lens.

3. A device according to claim 1, wherein said laser energy absorbing optical lens-shaped portion is in the shape of a negative optical lens.

4. A device according to claim 1, wherein said central axis of said laser energy absorbing optical lens-shaped portion is aligned with said central axis of said laser beam.

5. A device for modifying the surface of an optical element to vary its refractive power, the combination comprising:

means for generating a laser beam, said laser beam having a central axis and an outer periphery;

laser energy attenuator means, aligned to intercept said laser beam, for varying the energy distribution of said laser beam between said central axis and said outer periphery of said laser beam without refracting said laser beam within said laser energy attenuator means; and means for supporting the optical element in a position to intercept said laser beam after said laser beam has been intercepted by said laser energy attenuator means, said laser energy attenuator means including a laser energy absorbing optical portion in the shape of a lens having a central axis, having two opposed, regular surfaces intercepting said laser beam, at least one of said opposed surfaces being curved, and having an axial thickness that varies radially of said central axis thereof in a predetermined manner in proportion to the desired change in refractive power of the optical element.

6. A device according to claim 5, wherein said laser energy attenuator means comprises a first optical portion having a central axis and being transparent to said laser beam, a second optical portion having a central axis and being transparent to said laser beam, and a central optical portion forming said laser energy absorbing optical portion.

7. A device according to claim 6, wherein said central axes of said first, second and central portions are coaxially aligned and are coaxially aligned with said laser beam central axis.

8. A device according to claim 7, wherein said first, second and central portions have the same refractive index.

9. A device according to claim 6, wherein said first optical portion has a planar surface perpendicular to the central axis of said first optical portion, and said second optical portion has a planar surface perpendicular to the central axis of said second optical portion.

10. A device according to claim 6, wherein
said first optical portion is plano-concave,
said second optical portion is plano-concave, and
said central optical portion is bi-convex.

11. A device according to claim 6, wherein
said first optical portion is plano-convex,
said second optical portion is plano-convex, and
said central optical portion is bi-concave.

12. A device according to claim 6, wherein
said first and central optical portions engage one another, and
said second and central optical portions engage one another.

13. A device according to claim 5, wherein
said central axis of said laser energy absorbing optical portion is aligned with said central axis of said laser beam.

14. A device according to claim 5, wherein
said laser energy absorbing optical portion is in the shape of a positive lens.

15. A device according to claim 5, wherein
said laser energy absorbing optical portion is in the shape of a negative lens.

16. A device according to claim 5, wherein said laser energy attenuator means includes
means for reducing the energy of the laser beam from said central axis towards said outer periphery of said laser beam.

17. A device according to claim 5, wherein said laser energy attenuator means includes
means for reducing the energy of the laser beam from said outer periphery towards said central axis of said laser beam.

18. A device according to claim 5, and further comprising
means for cooling said laser energy attenuator means.

19. A device according to claim 5, wherein
said laser energy absorbing optical portion has material uniformly distributed therein that absorbs laser energy from said laser beam.

20. A method of modifying the surface of an optical element to vary its refractive power, comprising the steps of generating a laser beam having a central axis and an outer periphery, varying the energy distribution of the laser beam between the central axis and the outer periphery thereof, and intercepting the varied laser beam with the optical element, the varying step including passing the laser beam through a lens-shaped optical portion.

21. A method according to claim 20, wherein the varying step comprises the step of
preventing refraction of the laser beam.

22. A method according to claim 20, wherein the varying step comprises the step of
reducing the energy of the laser beam from the central axis towards the outer periphery thereof.

23. A method according to claim 20, wherein the varying step comprises the step of
reducing the energy of the laser beam from the outer periphery towards the central axis thereof.

* * * * *